(12) United States Patent
Chen et al.

(10) Patent No.: US 9,829,474 B2
(45) Date of Patent: Nov. 28, 2017

(54) ACETATE COMPLEXES AND METHODS FOR ACETATE QUANTIFICATION

(71) Applicant: GENERAL ELECTRIC COMPANY, Schenectady, NY (US)

(72) Inventors: Rui Chen, Clifton Park, NY (US); Andrew Michael Leach, Clifton Park, NY (US); Manuel Alfred Palacios, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 132 days.

(21) Appl. No.: 14/884,992

(22) Filed: Oct. 16, 2015

(65) Prior Publication Data
US 2017/0108481 A1  Apr. 20, 2017

(51) Int. Cl.
*G01N 33/00* (2006.01)
*G01N 33/15* (2006.01)
*C07F 15/02* (2006.01)
*G01N 21/31* (2006.01)

(52) U.S. Cl.
CPC .......... *G01N 33/15* (2013.01); *C07F 15/025* (2013.01); *G01N 21/31* (2013.01)

(58) Field of Classification Search
CPC ..................................................... G01N 33/15
USPC ..................................................... 436/129
See application file for complete search history.

(56) References Cited

U.S. PATENT DOCUMENTS

| 4,035,239 A | 7/1977 | McCloskey |
| 7,519,492 B2 | 4/2009 | Miller et al. |
| 7,610,157 B2 | 10/2009 | Miller et al. |
| 7,633,290 B1 | 12/2009 | Al-Khalidy et al. |
| 7,803,320 B2 | 9/2010 | Miller et al. |
| 8,731,640 B2 | 5/2014 | Urbahn et al. |
| 8,763,410 B2 | 7/2014 | Whitt et al. |

OTHER PUBLICATIONS

Fotouh R. Mansour, Neil D. Danielson "Ligand exchange spectrophotometric method for the determination of mole ratio in metal complexes" Microchemical Journal 103 (2012) 74-78.*
Xuan Xie, Yunwen Wu, Yiyang Kong, Zixiao Zhang, Xiaodong Zhou "Synthesis and characterization of multilayer core-shell structure hollow spheres with low density, favorable magnetic and conductive properties" Colloids and Surfaces A: Physicochem. Eng. Aspects 408 (2012) 104-113.*
Technical Bulletin, Acetate Colorimetric Assay Kit, Sigma-Aldrich, Catalog No. MAK086, pp. 1-3 2014.
(Continued)

*Primary Examiner* — Christine T Mui
*Assistant Examiner* — Emily Berkeley
(74) *Attorney, Agent, or Firm* — Pabitra K. Chakrabarti

(57) ABSTRACT

The present invention is directed to methods of acetate quantification and acetate complexes useful in the methods of acetate quantification. Such methods and complexes are useful for any application where acetate quantification is desired, including measuring of concentration of $^{13}C$ hyperpolarized acetate for imaging agent quality control in MRI and NMR spectroscopy. The disclosed acetate complexes may be prepared from acetate, $Fe^{3+}$, and sulfosalicylic acid and from acetate, $Fe^{3+}$, and salicylic acid.

19 Claims, 6 Drawing Sheets

(56) References Cited

OTHER PUBLICATIONS

Nishizawa, et al; "Anion Sensing by a Thiourea Based Chromoionophere via Hydrogen Bonding," Analytical Sciences, Jun. 1998, pp. 595-597, vol. 14.

Ferguson, et al; "Simultaneous Spectrophotometric Determination of Calcium and Magnesium with Chlorophosphonazo III," Analytical Chemistry, Apr. 1964, pp. 796-799, vol. 36, No. 4.

Pozdnyakov, et al; "Photochemistry of Fe(III) and sulfosalicylic acid aqueous solutions," Journal of Photochemistry and Photobiology A: Chemistry, 2006, pp. 75-81, vol. 182.

Foley, et al; "Spectrophotometric Studies on Complex Formation with Sulfosalicylic Acid. I. With Iron III," Spectrophotometry of Ferric Sulfosalicylate Complexes, Mar. 1948, vol. 70, pp. 1195-1197.

Foley, et al; "Spectrophotometric Studies on Complex Formation with Sulfosalicylic Acide. IV. With Iron (III) at Higher pH Values," Spectrophotometry of Iron(III)—Sulfosalicylic Acid Complexes, Dec. 1950, pp. 5609-5612, vol. 72.

Hu, et al; "A novel colorimetric and fluorescent chemosensor for acetate ions in aqueous media based on a rhodamine 6G-phenylurea conjugate in the presence of Fe(III) ions," The Royal Society of Chemistry, Chem. Commun., 2011, pp. 1622-1624, vol. 47.

Chung, et al; "Feasibility of monitoring acetic acid process using near-infrared spectroscopy," Vibrational Spectroscopy, 2003, pp. 125-131, vol. 31.

Jensen, et al; "Real-Time DNP NMR Observations of Acetic Acid Uptake, Intracellular Acidification, and of Consequences for Glycolysis and Alcoholic Fermentation in Yeast," Chemistry—A European Journal, 2013, pp. 13288-13293, vol. 19.

Jensen, et al; "Tissue-specific Short Chain Fatty Acid Metabolism and Slow Metabolic Recovery after Ischemia from Hyperpolarized NMR in vivo," Journal of Biological Chemistry, Dec. 25, 2009, pp. 36077-36082, vol. 284, No. 52.

* cited by examiner

ACETATE COMPLEXES AND METHODS FOR ACETATE QUANTIFICATION

FIELD OF THE INVENTION

This invention relates to methods of acetate quantification and acetate complexes useful in the methods of acetate quantification. Such methods and complexes are useful for any application where acetate quantification is desired, including measuring of concentration of $^{13}C$ hyperpolarized acetate for imaging agent quality control for use in MRI and NMR spectroscopy.

BACKGROUND OF THE INVENTION

Quality control ("QC") analysis of pharmaceutical products is an essential task that helps to ensure the safety of products used in the field of health care and eliminate the risk of an out of specification product making its way into a patient. In some instances, QC of a pharmaceutical product must be performed shortly after preparation of the product and immediately prior to injection into a patient. One example of a pharmaceutical product whose final preparation occurs immediately prior to injection is a hyperpolarized imaging agent for use in MRI and NMR spectroscopy. Hyperpolarizing of an imaging agent for use in MRI and NMR spectroscopy is done to increase sensitivity in the imaging agent; however, such hyperpolarizing can only be performed immediately prior to injection of the imaging agent into a patient, as the hyperpolarized imaging agent has a very short life span. That is, the imaging agent must be quickly transferred from its production source to its place of intended end use (i.e., injection into a patient) within a matter of minutes. For such a product, QC analysis performed immediately prior to injection is the only option. Additionally, QC analysis must be performed in a short period of time, without introducing any additional chemicals to the patient, and preserving the sterility of the pharmaceutical product. Devices for such QC analysis are known and their description could be found, for example, in U.S. Pat. Nos. 7,803,320, 7,519,492, and 7,610,157.

A common hyperpolarized imaging agent is $^{13}C_1$-pyruvate, as disclosed, for example, in U.S. Pat. Nos. 8,731,640, 8,763,410, and 7,633,290. In addition to pyruvate, acetate is known to be important for a number of metabolic processes. However, unlike pyruvate which can be readily measured by its ultraviolet absorption, acetate has no such absorption for QC purposes. An almost instant and strong signal from acetate agent is critical to meet $^{13}C$ QC requirements. There is a known assay for acetate which utilizes an enzyme based detection method, as described, for example, in U.S. Pat. No. 4,035,239. However, enzyme based acetate assay methods are time consuming, which makes them not suitable for QC of hyperpolarized acetate due to a very short life span of hyperpolarized acetate. Additionally, enzyme based acetate assay methods are expensive. Furthermore, extra calibration steps using known acetate standards are usually required due to stability and activity difference for enzyme batches.

The literature also reports a colorimetric and fluorescent assay for acetate ions based on a rhodamine 6G-phenylurea (RGPU) conjugate in the presence of Fe(III) ions. (Hu et al., Chem. Commun., 47: 1622-1624 (2011)). In this assay, the addition of acetate ion prompts dissociation of RGPU-Fe complex and release of free RGPU, which results in change in fluorescence and color shift from pink to colorless. The reaction media of this RGPU based assay is a 1:1 mixture of water and acetonitrile and the detectable acetate concentration range is 0-200 nM. However, this concentration range is about six orders of magnitude lower than desired for QC of hyperpolarized imaging agents. In addition, this RGPU based assay will not work in 100% aqueous solution and, therefore requires multiple dilution steps to adjust acetate concentration and to adjust properties of a liquid composition containing acetate for optimal assay conditions. Therefore, the RGPU based method is cumbersome, time-consuming, and unreliable. Accordingly, there is a need for quick and inexpensive acetate assay methods which preferably use water as a solvent. The methods and complexes disclosed herein solve this need and may be used for assaying acetate in a wide variety of applications, including but not limited to assays of hyperpolarized acetate imaging agent.

SUMMARY OF THE INVENTION

Embodiments of the present invention overcome the above-discussed disadvantages associated with the conventional acetate assay methods.

We have discovered novel acetate complexes that are useful for acetate quantification. Accordingly, in one embodiment, the invention is directed to an acetate complex, wherein the acetate complex comprises acetate, $Fe^{3+}$, and a compound of formula (Ia):

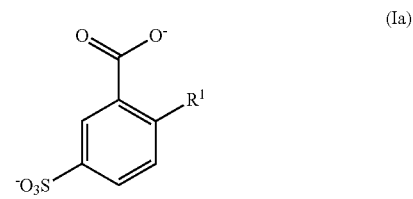

or a compound of formula (Ib):

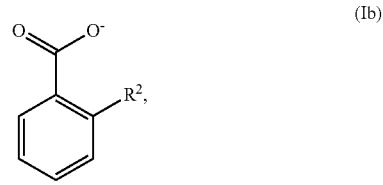

wherein $R^1$ is —OH or —O$^-$; and $R^2$ is —OH or —O$^-$.

In another embodiment, the invention is directed to a composition comprising an acetate complex and a solvent, wherein the acetate complex comprises acetate, $Fe^{3+}$, and a compound of formula (Ia):

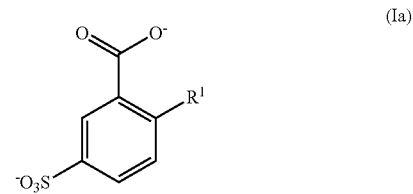

or a compound of formula (Ib):

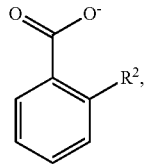
(Ib)

wherein $R^1$ is —OH or —O$^-$; and $R^2$ is —OH or —O$^-$.

In another embodiment, the invention is directed to a method for determining concentration of acetate in a sample, the method comprising: contacting the sample with $Fe^{3+}$ and an acid compound, wherein the acid compound is selected from the group consisting of sulfosalicylic acid and salicylic acid, whereby forming an acetate complex; wherein, when the acid compound is sulfosalicylic acid, the acetate complex comprises acetate, $Fe^{3+}$, and a compound of formula (Ia):

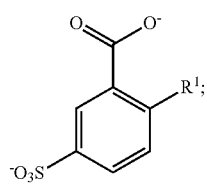
(Ia)

and wherein, when the acid compound is salicylic acid, the acetate complex comprises acetate, $Fe^{3+}$, and a compound of formula (Ib):

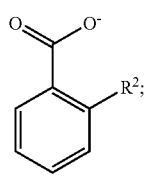
(Ib)

wherein $R^1$ is —OH or —O$^-$; and $R^2$ is —OH or —O$^-$; and photometrically measuring the acetate complex to determine concentration of acetate in the sample.

In another embodiment, the invention is directed to a method for determining concentration of $^{13}C$ hyperpolarized acetate in a sample, the method comprising: contacting the sample with $Fe^{3+}$ and an acid compound, wherein the acid compound is selected from the group consisting of sulfosalicylic acid and salicylic acid, whereby forming an acetate complex; wherein, when the acid compound is sulfosalicylic acid, the acetate complex comprises $^{13}C$ hyperpolarized acetate, $Fe^{3+}$, and a compound of formula (Ia):

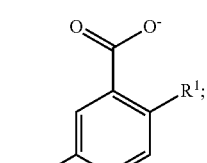
(Ia)

and wherein, when the acid compound is salicylic acid, the acetate complex comprises $^{13}C$ hyperpolarized acetate, $Fe^{3+}$, and a compound of formula (Ib):

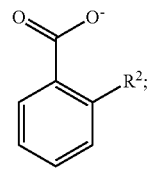
(Ib)

wherein $R^1$ is —OH or —O$^-$; and $R^2$ is —OH or —O$^-$; and photometrically measuring the acetate complex to determine concentration of $^{13}C$ hyperpolarized acetate in the sample.

Advantageously, the methods in accordance with the embodiments of the present invention are inexpensive, compatible with current pyruvate based quantification platforms, and allow for both quick and accurate acetate quantification. Moreover, the methods in accordance with the embodiments of the present invention may be conveniently used with water as a solvent.

The described herein novel and advantageous features of the acetate complexes and methods in accordance with embodiments of the present invention overcome shortcomings of the conventional acetate assay methods.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION OF THE INVENTION

Figure 1:
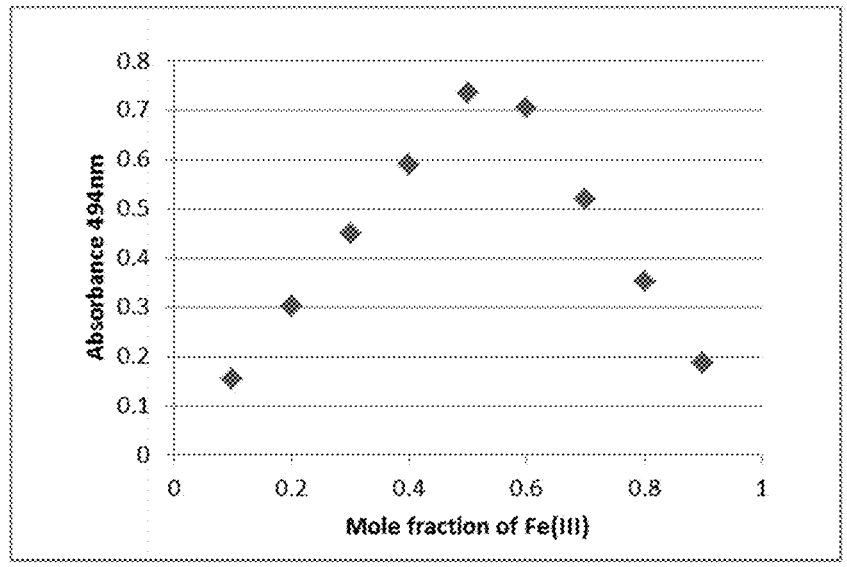
FIG. 1 shows a Job plot of $Fe^{3+}$/SSA complex in water solution.

In the following specification and the claims which follow, reference will be made to a number of terms, which shall be defined to have the following meanings.

The singular forms "a", "an", and "the" include plural referents unless the context clearly dictates otherwise.

Approximating language, as used herein throughout the specification and claims, may be applied to modify any quantitative representation that could permissibly vary without resulting in a change in the basic function to which it is related. Accordingly, a value modified by a term or terms, such as "about", is not to be limited to the precise value specified. In some instances, the approximating language may correspond to the precision of an instrument for measuring the value.

As used herein, the term "photometrically measuring" refers to any method of measuring light. Thus, photometrically measuring includes measuring light absorbance, including measuring light absorbance by colorimetric methods. Suitable methods for measuring light, including light absorbance, are known in the art. For example, an Ocean Optics fiber optics spectrometer may be used to measure absorbance and determine absorbance values. A well-plate reader, or a UV-Visible spectrometer may be used to measure absorbance. Furthermore, a light source such as LED and a photodetector such as photodiode may be used.

In the methods of the invention, the determination of acetate concentration from photometric measurement may be performed by using transfer function equations provided in the Examples section. The determination of acetate concentration from photometric measurement may also be performed by conducting experiments with reference samples having known acetate concentration to obtain a calibration curve. The obtained calibration curve may then be used to determine acetate concentration from a sample with an unknown acetate concentration.

As used herein, the term "apparatus designed for quality control of $^{13}C$ hyperpolarized acetate" refers to any apparatus that may be used in a QC of a hyperpolarized imaging agent, wherein the apparatus is equipped to photometrically measure at least one acetate complex disclosed herein. For example, a known hyperpolarized pyruvate QC apparatus may be adopted to photometrically measure at least one acetate complex disclosed herein. One potential example of such apparatus is described in Example 13.

The present invention relates to acetate assay methods and to acetate complexes useful in the disclosed acetate assay methods. In one embodiment, the invention is directed to an acetate complex comprising acetate, $Fe^{3+}$, and a compound of formula (Ia):

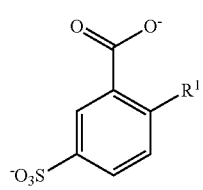

(Ia)

or a compound of formula (Ib):

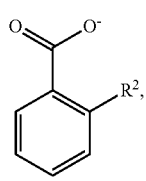

(Ib)

wherein $R^1$ is —OH or —O$^-$; and $R^2$ is —OH or —O$^-$.

In one embodiment, the acetate in the acetate complex is $^{13}C$ hyperpolarized acetate. In another embodiment, the acetate complex comprises acetate, $Fe^{3+}$, and a compound of formula (Ia). In yet another embodiment, the acetate complex has formula [acetate]$_{3n}$([$Fe^{3+}$][compound of formula (Ia)])$_n$, wherein n is an integer from 1 to 3. Accordingly, n may be 1, 2, or 3.

In one embodiment, the acetate complex comprises acetate, $Fe^{3+}$, and a compound of formula (Ib). In another embodiment, the acetate complex has formula [acetate][$Fe^{3+}$][compound of formula (Ib)]. In yet another embodiment, the acetate complex may be of formula [acetate]$_m$[$Fe^{3+}$][compound of formula (Ib)]$_p$, wherein m is an integer from 1 to 3 and p is an integer from 1 to 3. Accordingly, m may be 1, 2, or 3. Furthermore, p may be 1, 2, or 3. Accordingly, in one embodiment, the acetate complex may be of formula [acetate][$Fe^{3+}$][compound of formula (Ib)]. In another embodiment, the acetate complex may be of formula [acetate]$_2$[$Fe^{3+}$][compound of formula (Ib)]$_2$. In yet another embodiment, the acetate complex may be of formula [acetate]$_3$[$Fe^{3+}$][compound of formula (Ib)]$_3$.

The present invention is also directed to compositions comprising disclosed herein complexes. In one embodiment, A composition comprising an acetate complex and a solvent, wherein the acetate complex comprises acetate, $Fe^{3+}$, and a compound of formula (Ia):

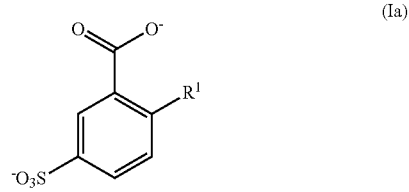

(Ia)

or a compound of formula (Ib):

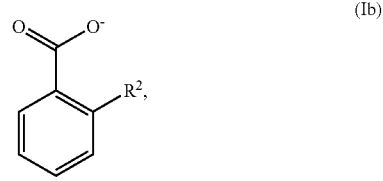

(Ib)

wherein $R^1$ is —OH or —O$^-$; and $R^2$ is —OH or —O$^-$.

In one embodiment, the acetate in the compositions of the invention is $^{13}C$ hyperpolarized acetate.

In one embodiment, the acetate complex of the compositions of the invention comprises acetate, $Fe^{3+}$, and a compound of formula (Ia). In another embodiment, the acetate complex has formula [acetate]$_{3n}$([$Fe^{3+}$][compound of formula (Ia)])$_n$, wherein n is an integer from 1 to 3. In one embodiment, n is 1. In another embodiment, n is 2. In yet another embodiment, n is 3.

In another embodiment, the acetate complex of the compositions of the invention comprises acetate, $Fe^{3+}$, and a compound of formula (Ib). In one embodiment, the acetate complex has formula [acetate][$Fe^{3+}$][compound of formula (Ib)]. In yet another embodiment, the acetate complex may be of formula [acetate]$_m$[$Fe^{3+}$][compound of formula (Ib)]$_p$, wherein m is an integer from 1 to 3 and p is an integer from 1 to 3. Accordingly, m may be 1, 2, or 3. Furthermore, p may be 1, 2, or 3.

The compositions of the invention may further comprise ethylenediaminetetraacetic acid ("EDTA") and a metal ion, wherein the metal ion is selected from the group consisting of $Zn^{2+}$, $Cu^{2+}$, and mixtures thereof. In some embodiments, the compositions of the invention may include a buffer.

In one embodiment, the solvent in the compositions of the invention is an aqueous solvent. In another embodiment, the solvent in the compositions of the invention is water.

In another embodiment, the invention is directed to a method for determining concentration of acetate in a sample, the method comprising: contacting the sample with $Fe^{3+}$ and an acid compound, wherein the acid compound is selected from the group consisting of sulfosalicylic acid and salicylic acid, whereby forming an acetate complex; wherein, when the acid compound is sulfosalicylic acid, the acetate complex comprises acetate, $Fe^{3+}$, and a compound of formula (Ia):

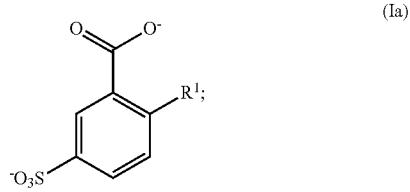

and
wherein, when the acid compound is salicylic acid, the acetate complex comprises acetate, $Fe^{3+}$, and a compound of formula (Ib):

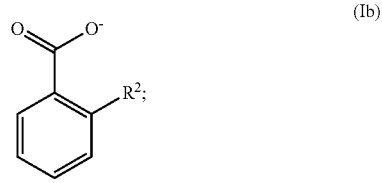

wherein $R^1$ is —OH or —O$^-$; and $R^2$ is —OH or —O$^-$; and photometrically measuring the acetate complex to determine concentration of acetate in the sample.

In one embodiment, acetate in the sample comprises $^{13}C$ hyperpolarized acetate. In another embodiment, the method is performed using an apparatus designed for quality control of $^{13}C$ hyperpolarized acetate.

In one embodiment, the acid compound is sulfosalicylic acid, and photometrically measuring comprises: measuring an absorbance value of the acetate complex at a light wavelength of from about 350 nm to about 550 nm; and determining concentration of acetate in the sample from the absorbance value of the acetate complex. The light wavelength used in this method may also be from about 430 nm to about 470 nm.

In one embodiment, the acid compound is salicylic acid, and photometrically measuring comprises: measuring an absorbance value of the acetate complex at a light wavelength of from about 400 nm to about 650 nm; and determining concentration of acetate in the sample from the absorbance value of the acetate complex. The light wavelength used in this method may also be from about 400 nm to about 520 nm.

The sample in the described methods may include acetate and an aqueous solvent. The sample may further include a buffer.

In one embodiment, the acetate complex of the methods disclosed herein may be of formula $[\text{acetate}]_{3n}([Fe^{3+}][\text{compound of formula (Ia)}])_n$, wherein n is an integer from 1 to 3. Accordingly, n may be 1, 2, or 3.

In another embodiment, the acetate complex of the methods disclosed herein may be of formula $[\text{acetate}][Fe^{3+}][\text{compound of formula (Ib)}]$. In another embodiment, the acetate complex may be of formula $[\text{acetate}]_m[Fe^{3+}][\text{compound of formula (Ib)}]_p$, wherein m is an integer from 1 to 3 and p is an integer from 1 to 3. Accordingly, m may be 1, 2, or 3. Furthermore, p may be 1, 2, or 3.

In one embodiment, contacting the sample with $Fe^{3+}$ and the acid compound comprises contacting the sample with a reagent composition, the reagent composition comprising a $Fe^{3+}$-sulfosalicylic acid complex or $Fe^{3+}$-salicylic acid complex. In one embodiment, the reagent composition is a liquid. In another embodiment, the reagent composition is a dry powder.

In one embodiment, the sample further comprises EDTA and the reagent composition further comprises a metal ion, wherein the metal ion is selected from the group consisting of $Zn^{2+}$, $Cu^{2+}$, and mixtures thereof. In one embodiment, the reagent composition further comprises a buffer.

In another embodiment, the invention is directed to a method for determining concentration of $^{13}C$ hyperpolarized acetate in a sample, the method comprising: contacting the sample with $Fe^{3+}$ and an acid compound, wherein the acid compound is selected from the group consisting of sulfosalicylic acid and salicylic acid, whereby forming an acetate complex; wherein, when the acid compound is sulfosalicylic acid, the acetate complex comprises $^{13}C$ hyperpolarized acetate, $Fe^{3+}$, and a compound of formula (Ia):

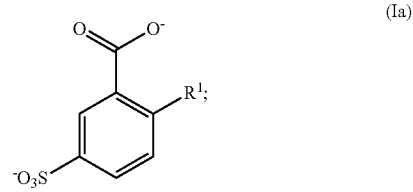

and
wherein, when the acid compound is salicylic acid, the acetate complex comprises $^{13}C$ hyperpolarized acetate, $Fe^{3+}$, and a compound of formula (Ib):

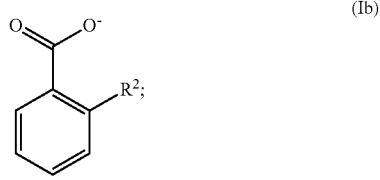

wherein $R^1$ is —OH or —O$^-$; and $R^2$ is —OH or —O$^-$; and photometrically measuring the acetate complex to determine concentration of $^{13}C$ hyperpolarized acetate in the sample.

In one embodiment, the method is performed using an apparatus designed for quality control of $^{13}C$ hyperpolarized acetate.

In one embodiment, the acid compound is sulfosalicylic acid, and photometrically measuring comprises: measuring an absorbance value of the acetate complex at a light wavelength of from about 350 nm to about 550 nm; and determining concentration of $^{13}C$ hyperpolarized acetate in the sample from the absorbance value of the acetate complex. The light wavelength used in this method may also be from about 430 nm to about 470 nm.

In another embodiment, the acid compound is salicylic acid, and photometrically measuring comprises: measuring an absorbance value of the acetate complex at a light wavelength of from about 400 nm to about 650 nm; and determining concentration of $^{13}C$ hyperpolarized acetate in the sample from the absorbance value of the acetate complex. The light wavelength used in this method may also be from about 400 nm to about 520 nm.

In one embodiment, the sample comprises $^{13}C$ hyperpolarized acetate and an aqueous solvent. In another embodiment, the sample further comprises a buffer.

In one embodiment, the acetate complex of the methods disclosed herein may be of formula $[^{13}C$ hyperpolarized acetate$]_{3n}([Fe^{3+}][$compound of formula (Ia)$])_n$, wherein n is an integer from 1 to 3. In one embodiment, n is 1. In another embodiment, n is 2. In yet another embodiment, n is 3.

In another embodiment, the acetate complex of the methods disclosed herein may be of formula $[^{13}C$ hyperpolarized acetate$][Fe^{3+}][$compound of formula (Ib)$]$. In yet another embodiment, the acetate complex may be of formula $[$acetate$]_m[Fe^{3+}][$compound of formula (Ib)$]_p$, wherein m is an integer from 1 to 3 and p is an integer from 1 to 3. Accordingly, m may be 1, 2, or 3. Furthermore, p may be 1, 2, or 3.

In one embodiment, contacting the sample with $Fe^{3+}$ and the acid compound comprises contacting the sample with a reagent composition, the reagent composition comprising a $Fe^{3+}$-sulfosalicylic acid complex or $Fe^{3+}$-salicylic acid complex. In one embodiment, the reagent composition is a liquid. In another embodiment, the reagent composition is a dry powder.

In one embodiment, the sample further comprises EDTA and the reagent composition further comprises a metal ion, wherein the metal ion is selected from the group consisting of $Zn^{2+}$, $Cu^{2+}$, and mixtures thereof. In one embodiment, the reagent composition further comprises a buffer.

This written description uses examples to disclose embodiments of the invention, including the best mode, and also to enable any person skilled in the art to practice the invention, including making and using any devices or systems and performing any incorporated methods. The patentable scope of the invention is not limited to the scope of the provided examples, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

EXAMPLES

Example 1

Job Plot of Fe/SSA Complex $Fe^{3+}$/SSA complex formation has been commonly used as a colorimetric method for iron quantification. Iron and SSA form a 1:1 violet complex in acidic media and shift to orange and yellow color as pH increases to neutral and basic range. In our studies, Fe/SSA reagents were prepared in water solutions which are acidic due to presence of SSA. Varying volumes of 1 mM $Fe^{3+}$ were mixed with 1 mM SSA solution, total volume was kept constant at 2 mL. The total molar concentration of $Fe^{3+}$ and SSA were held constant. An Ocean Optics fiber optics spectrometer set up and a UV-Vis light source were used for absorbance measurement. A Job plot was obtained by measuring the absorbance change with continuous varying of the mole ratio of $Fe^{3+}$, as shown in FIG. 1. For example, at Fe(III) ratio of 0.2, 0.4 mL 1 mM $Fe^{3+}$ was mixed with 1.6 mL 1 mM SSA solution. The peak absorbance at 490 nm reached a maximum at 0.5 mole ratio, which corresponds to 1:1 stoichiometry of $Fe^{3+}$ to SSA.

Example 2

Acetate, $Fe^{3+}$, and SSA Mixture Study

Figure 2:
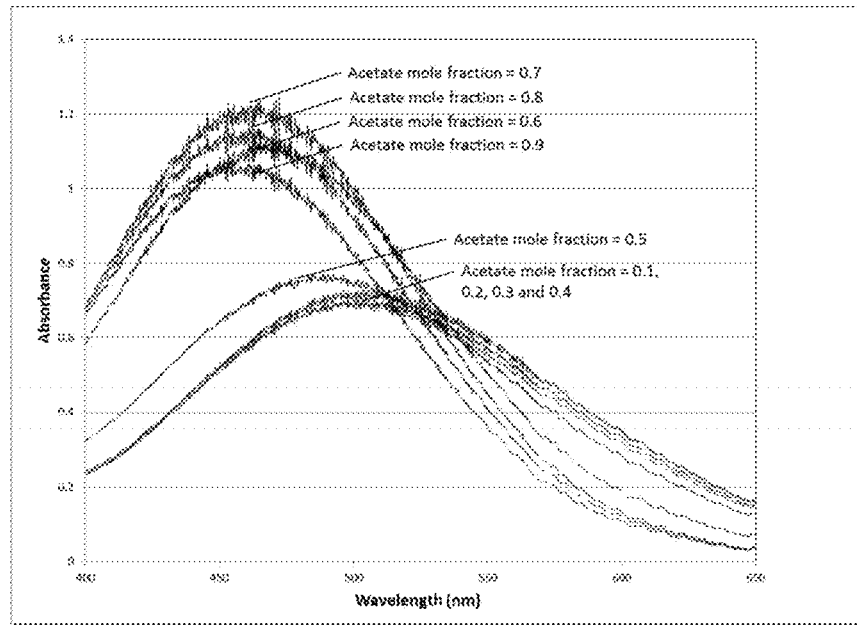
FIG. 2 shows an absorbance spectra of a series of Fe/SSA/acetate mixtures.

Mixing $Fe^{3+}$ with acetate alone did not generate any color, which was expected. Reagent A (0.5 mM $Fe^{3+}$, 200 mM acetate) and reagent B (0.5 mM $Fe^{3+}$, 200 mM SSA) were mixed at varying mole ratios to study mixtures of acetate, $Fe^{3+}$, and SSA. For example, at mole ratio of acetate at 0.2, 0.4 mL reagent A was mixed with 1.6 mL reagent B. Iron concentration was kept constant with respect to the total concentration of the combination of SSA and acetate. The results are shown in FIG. 2. As could be seen in FIG. 2, when the mole fraction of acetate was less than 0.5, the absorbance spectra had absorbance maximum at 490 nm, which was consistent with Fe/SSA complex absorbance. With increasing mole fraction of acetate, the absorbance maximum shifted to 470 nm. The peak absorbance increased first, then decreased once the mole fraction was bigger than 0.7. The data points within the mole fraction range of 0.5 to 1.0 were fitted with second degree polynomial function, which yielded a maximum at 0.75 mole ratio. This corresponded to a complex of acetate, $Fe^{3+}$, and SSA ("acetate/Fe/SSA complex") having a molar ratio of 3 moles of acetate per 1 mole of $Fe^{3+}$ per 1 mole of SSA (i.e., a molar ratio of 3:1:1 of acetate:$Fe^{3+}$:SSA).

Figure 3:
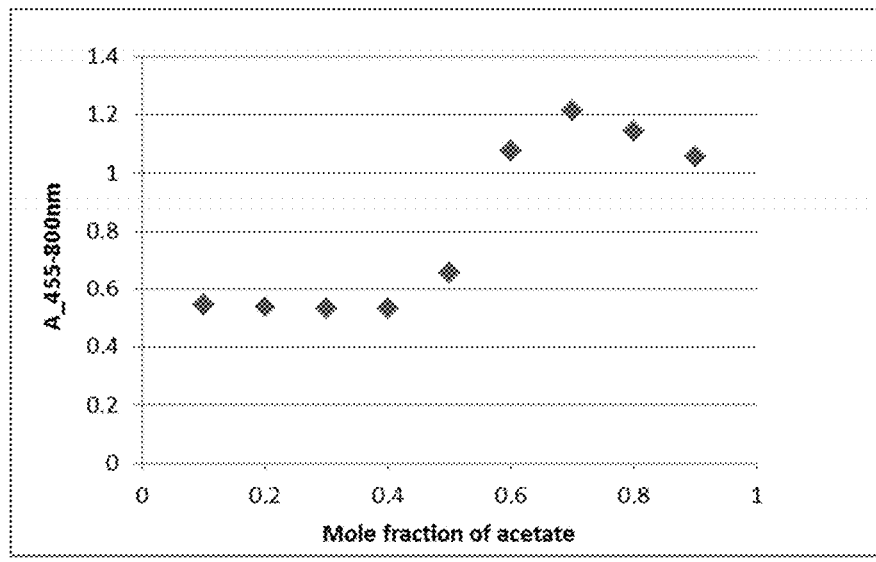
FIG. 3 shows a Job plot of 450 nm absorbance vs. mole fraction of acetate.

$Fe^{3+}$ concentration was kept within 0.5-0.65 mM range in order to have a relatively large absorbance signal while not going beyond 99% absorbance (A=2) for accuracy and reproducibility considerations. FIG. 3 shows that the largest absorbance change vs. acetate concentration was achieved with acetate's mole fraction increasing between 0.5 and 0.7. Since the required acetate quantification concentration range is 200-300 mM, the optimal SSA concentration for this concentration range of acetate was calculated to be at 130-200 mM.

Example 3

Preparation of Acetate/Fe/SSA Complex $Fe^{3+}$ and sulfosalicylic acid ("SSA") reagent ("Fe/SSA reagent") was prepared by dissolving $FeCl_3$ and 5-sulfosalicylic acid dihydrate in water to a final concentration of 0.65 mM $Fe^{3+}$ and 200 mM SSA. The Fe/SSA reagent solution was acidic due to presence of SSA.

Acetate standards were prepared by dilution of acetic acid to basic buffers containing Tris and sodium hydroxide. For example, 5 g acetic acid was mixed with 83.6 g basic buffers (720 mM NaOH and 400 mM TRIS), and 110 g dilution medium (0.1% EDTA in water) to make final acetate stock solution of ~410 mM acetate stock solution at pH 7.6. The acetate stock solution was then diluted with dilution medium to make 200-300 mM acetate samples as needed.

Solutions of an acetate complex of acetate, $Fe^{3+}$ and SSA ("acetate/Fe/SSA complex"), were prepared by mixing the Fe/SSA reagent solutions (1 mL) with aqueous solutions of acetate standards (1 mL) in 1:1 volume ratio.

Example 4

Acetate/Fe/SSA Complex for Acetate Quantification—Spectroscopy Measurement

Figure 4:
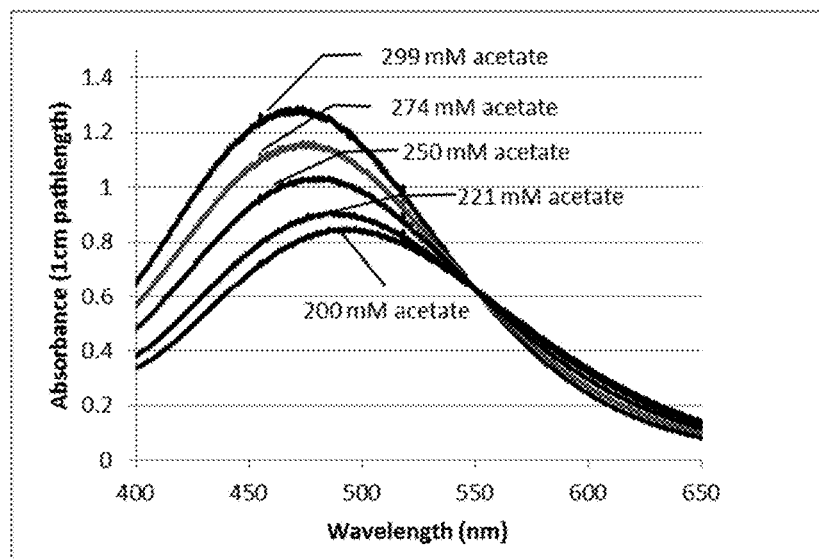
FIG. 4 shows an absorbance spectra of acetate/Fe/SSA complexes.

Acetate quantification was done by absorbance measurement of the solutions of acetate/Fe/SSA complex prepared in Example 3. The absorbance measurement was performed through 1 cm path length cuvette. An Ocean Optics fiber optics spectrometer (USB4000) and a UV-Vis light source were used for initial evaluation. During gauge and transfer function studies, an LED-photodiode (PD) based QC plates designed for pyruvic acid detection in a commercial system were used. Specifically, 1 cm path length TOPAS® cuvette (irradiated and aged), channel 4 LED (450 nm) and channel 3 PD detection were used. Results of the absorbance measurements are shown in FIG. 4.

Example 5

Figure 5:
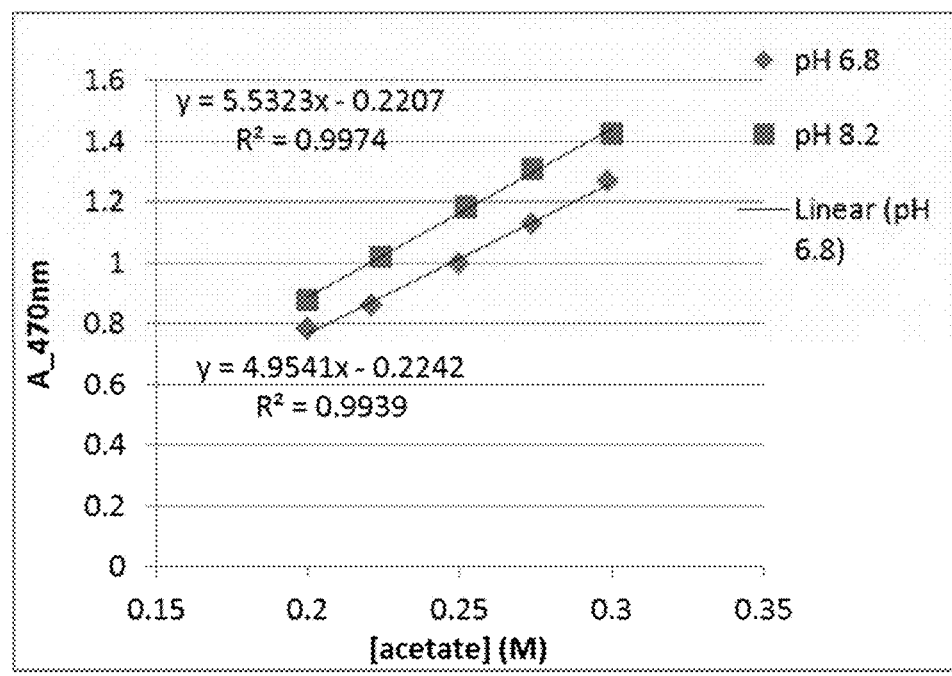
FIG. 5 shows calibration curves of acetate standards at two different pH conditions based on the absorbance of acetate/Fe/SSA complex.

Acetate/Fe/SSA Complex for Acetate Quantification—Calibration for Determination of Acetate Concentration FIG. 5 shows calibration curves of acetate standards based on the absorbance values of acetate/Fe/SSA complex at pH 6.8 and 8.2. During preparation of 400 mM acetate stock solution, varying amount of neutralization buffer was mixed with acetic acid to reach final pH of 6.8 and 8.2, Then 400 mM acetate stock solutions were diluted to five different concentrations between 200 to 300 mM. 1 mL quantities of these acetate solutions were mixed with 1 mL Fe/SSA reagent, and absorbance was measured by an Ocean Optics fiber optics spectrometer set up.

Example 6

Acetate/Fe/SSA Complex for Acetate Quantification—Gage and Transfer Function Study Central composite (Response Surface) design was used to study the experimental factors and determine the transfer function to calibrate acetate concentrations using QC module (Table 1). A total of 50 runs were performed in random order within each temperature block, and the sequence of running each temperature block was randomized as well. EPA stands for Electron Paramagnetic Agent, and the EPA in this study was Tris(8-carboxyl-2,2,6,6-tetra(2-(1-methoxy-2,2-d2-ethyl))-benzo[1,2-d:4,5-d']bis(dithiole-4-yl)methyl sodium salt. It was present in final dissolved polarized acetate solution and due to its absorbance in the visible range, it was included in the DOE. We took into consideration temperature sensitivity of Tris buffer (−0.03 pH/degree), which was used for pH adjustment. pH values of all standards were adjusted at room temperature to correspond to desired experimental design at 30° C. For example, an acetate standard was adjusted to pH=7.47 at 21° C., which corresponds to pH=7.2 at 30° C. The absorbance values for the design of experiment ("DOE") were imported to DESIGN-EXPERT (version 8.0.6) for analysis. No transformation was made. Table 1 provides information on the experimental parameters settings based on Central composite (Response Surface) design.

TABLE 1

Central composite designs for acetate quantification study.

| Name | Low | High | Axial point_low | Axial point_high |
|---|---|---|---|---|
| Acetate concentration (M) | 0.23 | 0.27 | 0.202 | 0.298 |
| pH | 7.2 | 7.8 | 6.8 | 8.2 |
| Temperature (° C.) | 31 | 35.5 | 27.9 | 38.6 |
| [EDTA] (g/L) | 0.098 | 0.102 | 0.095 | 0.105 |
| [EPA] (μM) | 1.2 | 2.8 | 0.1 | 3.9 |

Table 2 shows ANOVA analysis results of the DOE runs. Acetate concentration, pH, temperature, acetate concentration*pH and $pH^2$ were found to be significant. EPA was not significant, most likely due to the large absorbance contribution from acetate/Fe/SSA complex. EDTA with ±2% variation in concentration was found to be not significant either. A good agreement between $R^2$ (0.9920) and $R^2_{adjusted}$ (0.9911) suggested that the terms used in the transfer function are significant. An agreement between $R^2$ (0.9920) and $R^2_{predicted}$ (0.9888) indicated that quality of the model is very high.

The transfer function was used to predict acetate concentration based on measured absorbance value for 50 points. Residual Standard Deviation (RSD), specifically, $RSD_{250\ mM}$, was calculated to be 0.7% (1.8 mM) (Table 3, FIG. 6). If temperature input is to be removed from the transfer function, the equation is adjusted slightly (see Table 2). $RSD_{250\ mM}$ was calculated to be slightly worse to 0.8% (2 mM), but it is still well within the 3% of the specification.

TABLE 2

Analysis of acetate QC based on acetate/Fe/SSA complex, including ANOVA analysis statistics of significant factors and transfer function.
Analysis of variance table [Partial sum of squares - Type III]

| Source | Sum of Squares | df | Mean Square | F Value | p-value Prob > F | |
|---|---|---|---|---|---|---|
| Model | 0.60 | 5 | 0.12 | 1095.48 | <0.0001 | significant |
| A-Acetate conc | 0.51 | 1 | 0.51 | 4682.28 | <0.0001 | significant |
| B-pH | 0.072 | 1 | 0.072 | 660.75 | <0.0001 | significant |
| C-temperature | 7.495E−004 | 1 | 7.495E−004 | 6.88 | 0.0119 | significant |
| AB | 1.179E−003 | 1 | 1.179E−003 | 10.82 | 0.0020 | significant |
| $B^2$ | 0.013 | 1 | 0.013 | 116.67 | <0.0001 | Significant |
| Residual | 4.795E−003 | 44 | 1.090E−004 | | | |

TABLE 2-continued

Analysis of acetate QC based on acetate/Fe/SSA complex, including
ANOVA analysis statistics of significant factors and transfer function.
Analysis of variance table [Partial sum of squares - Type III]

| Source | Sum of Squares | df | Mean Square | F Value | p-value Prob > F | |
|---|---|---|---|---|---|---|
| Lack of Fit | 4.310E−003 | 37 | 1.165E−004 | 1.68 | 0.2443 | Not significant |
| Pure Error | 4.852E−004 | 7 | 6.931E−005 | | | |
| Cor Total | 0.60 | 49 | | | | |

R-Squared = 0.9920
Adj R-Squared = 0.9911
Pred R-Squared = 0.9888
Equation:
1. [acetate] = (9.675 − Abs − 2.5746 * pH − 1.85E−03 * temperature + 0.164 * pH$^2$)/(2.162 − 1.012 * pH)
2. With elimination of temperature factor, [acetate] = (9.6139 − Abs − 2.5746 * pH + 0.164 * pH^2)/(2.162 − 1.012 * pH)

Table 2 lists the analysis results from DESIGN-EXPERT®, including factors that are significant for acetate quantification, how well the model fits the experiment data and transfer function to derive acetate concentration based on input factors, such as Abs, pH, temperature, etc.

The symbols in equations 1 and 2 of Table 2 have the following meanings:
"[acetate]" has a meaning of "molar concentration of acetate";
"−" symbol has a meaning of "minus"
"+" symbol has a meaning of "plus";
"E−03" has a meaning of "multiplication by $10^{−3}$", i.e., "multiplication by 0.001";
"Abs" abbreviation has a meaning of "absorbance";
"pH" has a meaning of "a pH value of the solution containing the acetate/Fe/SSA complex";
"temperature" has a meaning of "a temperature (° C.) of the solution containing the acetate/Fe/SSA complex";
"*" symbol has a meaning of "multiplication";
"/" symbol has a meaning of "division"; and
"^" symbol has a meaning of "to the power of".

TABLE 3

Predicted acetate concentration based on the two calibration equations from Table 2.

| | Prediction based on Equation1 | | | Prediction based on Equation2 (no temperature input) | | |
|---|---|---|---|---|---|---|
| Concentration (M) | average (M) | Stdev (M) | RSD | average (M) | Stdev (M) | RSD |
| 0.23 | 0.230 | 0.002 | 0.7% | 0.230 | 0.002 | 0.7% |
| 0.25 | 0.250 | 0.002 | 0.7% | 0.250 | 0.002 | 0.8% |
| 0.27 | 0.271 | 0.002 | 0.7% | 0.271 | 0.002 | 0.7% |

Table 3 demonstrates the relative errors introduced to acetate quantification when equation 1 or 2 from Table 2 was used. Table 3 shows that with elimination of temperature as one of the input parameters, the impact on acetate quantification is negligible.

Figure 6:
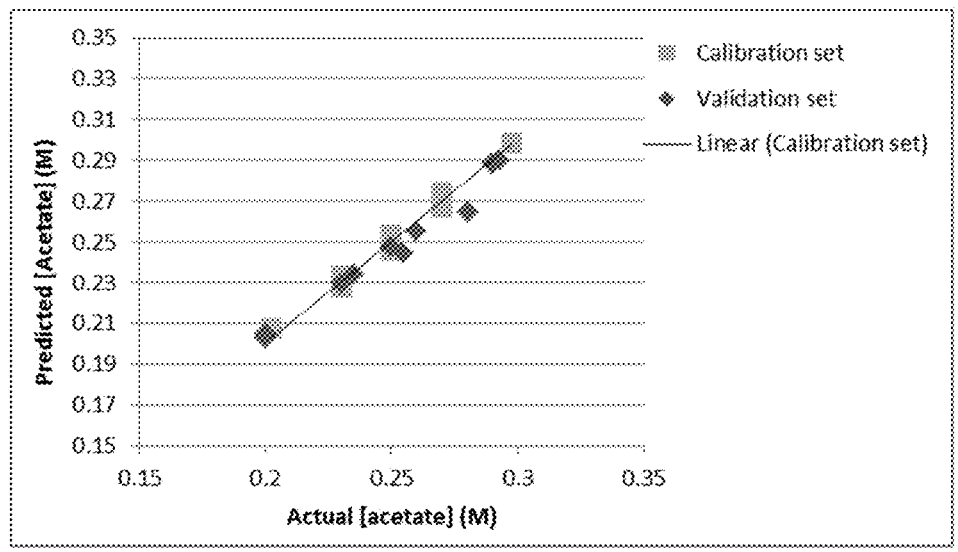
FIG. 6 shows a graphical representation of results of the transfer function study.

Additional 10 validation points were prepared spreading over a range of acetate concentration, pH and temperature. 10 acetate samples were prepared and then mixed 1:1 in volume with Fe/SSA reagent (1 mM Fe(NH$_4$)(SO$_4$)$_2$, 200 mM SSA). Equation 2 from Table 2 was used for the prediction. FIG. 6 plots both the 50 DOE points and 10 validation points. There was one validation sample with pH 6.8 deviating from the linear model more significantly than the other validation points, which might relate to poor buffering power at this pH. The RSD$_{250\ mM}$ for the validation set was calculated to be 2.66%, which is still within the 3% specification requirement (RSD$_{250\ mM}$ excluding the pH 6.8 data equals to 2%).

Transfer Function Study Using QC Optical Module

Figure 11:
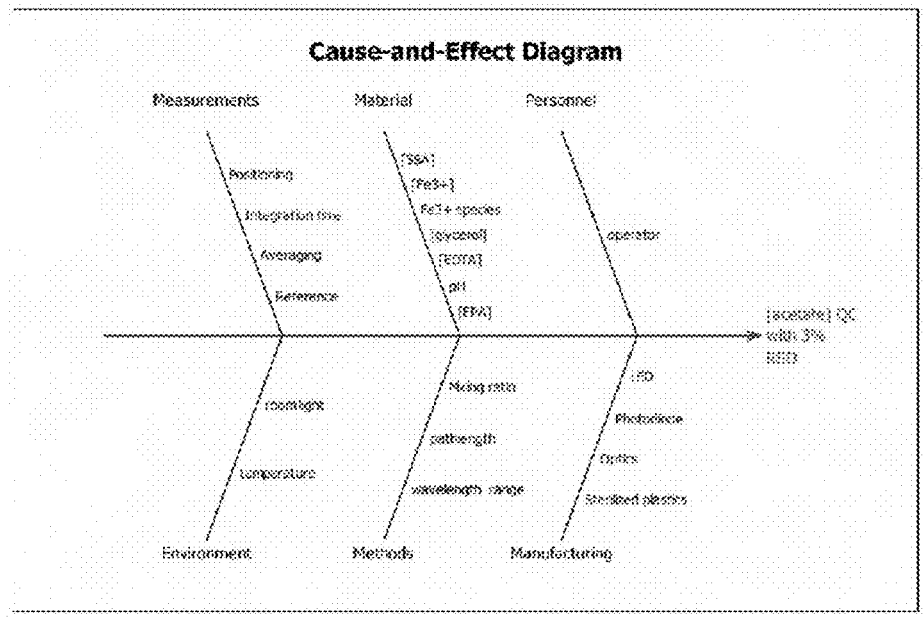
FIG. 11 shows a cause-and-effect diagram of factors influencing acetate QC method using QC optical module.

Although the light-emitting diode-photodiode module has been demonstrated to be sufficient to differentiate acetate concentration at gage study, there are many factors that may influence the detected absorbance signal leading to measurement errors. FIG. 11 is a cause-and-effect diagram listing a range of possible factors.

A series of experiments have been done to screen the factors before a full the design of experiment ("DOE"). pH and temperature are known factors. Glycerol at 1.2-1.8% was found not to affect absorbance signal significantly. EDTA is a strong complex agent, which will cause absorbance decrease when it complexes with $Fe^{3+}$ to form a colorless complex.

Presence of 0.1 g/L EDTA (0.27 mM) in dissolution media does not stop the formation of acetate/Fe/SSA complex, but 20% fluctuation of EDTA will have a significant impact. A possible mitigation to the EDTA fluctuation is to provide a second metal ion to complex with EDTA, therefore "buffering" out the EDTA noises. Addition of 200 mM ZnCl$_2$ has been demonstrated to decrease absorbance fluctuation to 0.08% if EDTA varies 20% in concentration. Later it was found that reaction mixtures containing ZnCl$_2$ have a slow decay (15% loss after 20 min). This is not a factor for QC methods since the detection will be done within seconds.

Example 7

Acetate/Fe/SSA Complex for Acetate Quantification—Compensation for EDTA Effect in Acetate Samples If EDTA is present in aqueous solutions of acetate samples and if EDTA concentration fluctuates from sample to sample by large percentage, this may influence acetate calibration. Adding metal ions, such as $Cu^{2+}$ and/or $Zn^{2+}$, can improve Fe/SSA reagent's robustness to EDTA fluctuation. The adjusted Fe/SSA reagent may include: 1 mM Fe(NH$_4$)(SO$_4$)$_2$, which is a source of 1 mM $Fe^{3+}$; 200 mM 5-sulfosalicylic acid; and 200 mM ZnCl$_2$. Another example of Fe/SSA reagent may include: 1 mM Fe(NH$_4$)(SO$_4$)$_2$; 200 mM 5-sulfosalicylic acid; and 200 mM CuCl$_2$. The Fe/SSA reagent would then be mixed 1:1 in volume with an aqueous solution of acetate sample (pH 6.8-8.2). For example, 1 mL of Fe/SSA reagent solution would be mixed with 1 mL of aqueous acetate sample.

Example 8

Acetate/Fe/SSA Complex for Acetate Quantification—Using Dried Fe/SSA Reagent

To simplify acetate quantification process, a fixed amount of Fe/SSA reagent can be aliquoted to an empty container or optical cuvette and allowed to dry at room temperature or on a heater. Dried Fe/SSA reagent may then be obtained. Subsequent addition of an aqueous solution of acetate sample will dissolve the dried Fe/SSA reagent powder and will result in formation of acetate/Fe/SSA complex. This procedure is suitable for field application and QC application. Dried Fe/SSA reagent is very water soluble, which facilitates for a quick reaction and fast measurement. For example, 1 mL of Fe/SSA reagent, such as an aqueous solution of 1 mM $Fe(NH_4)(SO_4)_2$ and 200 mM 5-sulfosalicylic acid, can be dried inside a 1 cm path length cuvette. Subsequent addition of 1-2 mL an aqueous solution of an acetate sample (pH 6.8-8.2) will result in formation of acetate/Fe/SSA complex for absorbance measurement and quantification of acetate in the sample. A smaller amount Fe/SSA reagent at higher concentration may also be used to speed up drying process.

Example 9

Job Plot of Fe/SA Complex

Figure 7:
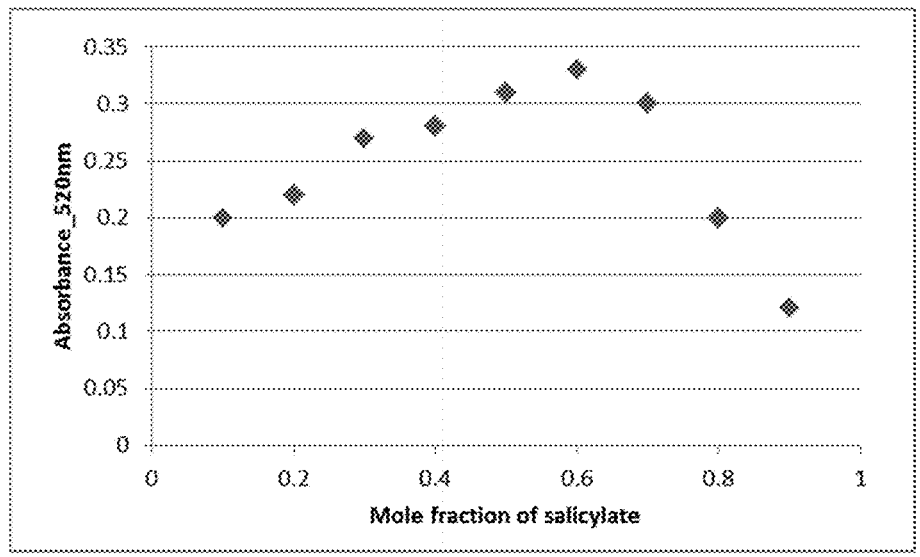
FIG. 7 shows a Job plot of $Fe^{3+}$/SA complex in water solution.

A Job plot shown in FIG. 7 was obtained by measuring an absorbance change while continuously varying the mole ratio of $Fe^{3+}$. The total molar concentration of $Fe^{3+}$ and salicylic acid ("SA") were held constant. Varying volumes of 1 mM $Fe^{3+}$ were mixed with 1 mM SA solution, total volume was kept constant at 2 mL. For example, at $Fe^{3+}$ mole ratio of 0.2, 0.4 mL 1 mM $Fe^{3+}$ were mixed with 1.6 mL 1 mM SA solution. An Ocean Optics fiber optics spectrometer set up and a UV-Vis light source were used for absorbance measurement. The peak absorbance at 520 nm reached maximum at mole ratio of SA between 0.6-0.7, which corresponds to 1:3 stoichiometry of Fe:SA.

Example 10

Acetate, $Fe^{3+}$, and SA Mixture Study

Figure 8:
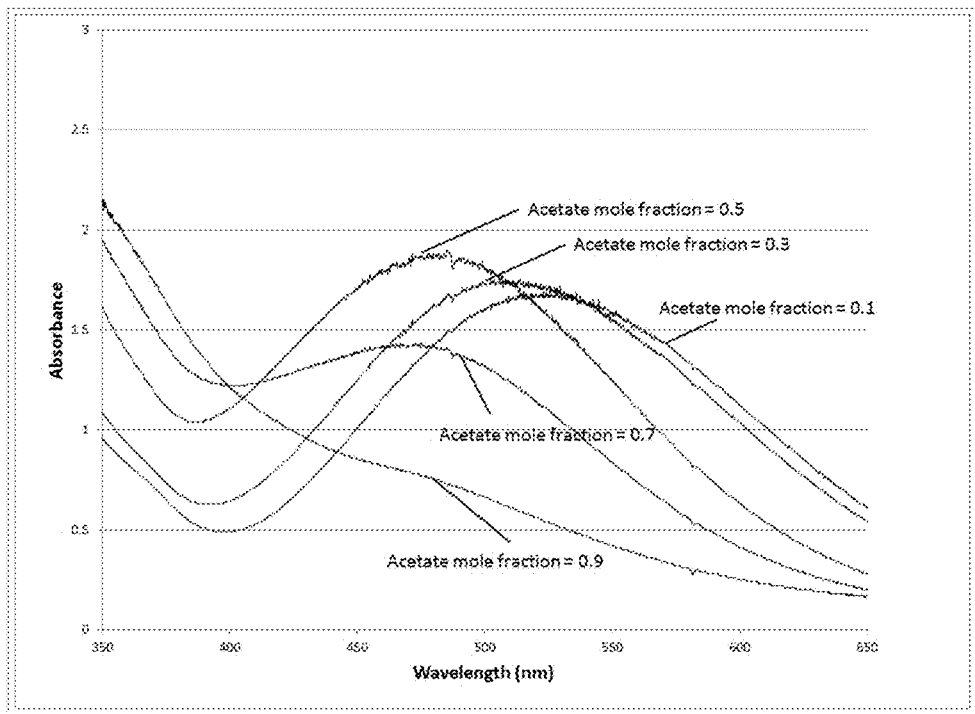
FIG. 8 shows absorbance spectra of a series of Fe/SA/acetate mixtures.

In order to study a complex of acetate, $Fe^{3+}$, and SA ("acetate/Fe/SA complex"), reagent A (1 mM $Fe^{3+}$, 15 mM acetate) and reagent B (1 mM $Fe^{3+}$, 15 mM SA) were mixed at varying mole ratios. Iron concentration and the total combined concentration of SA and acetate were kept constant. For example, at mole ratio of acetate at 0.2, 0.4 mL reagent A was mixed with 1.6 mL reagent B. An Ocean Optics fiber optics spectrometer set up and a UV-Vis light source were used for absorbance measurement. The results are shown in FIG. 8. With acetate addition, the absorbance maximum started to shift to lower wavelength (from 520 nm for $Fe^{3+}$/SA to 465 nm).

Figure 9:
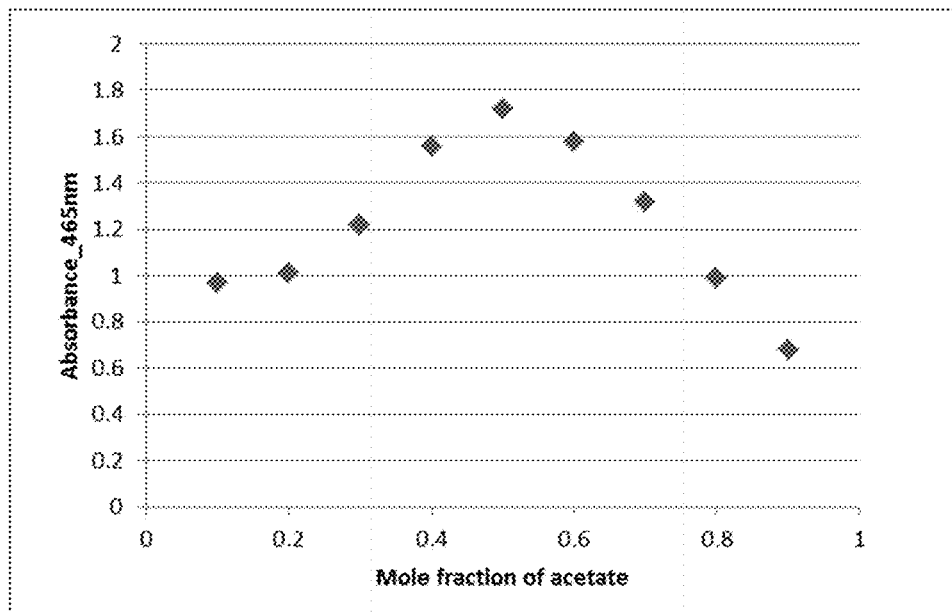
FIG. 9 shows a Job plot of 465 nm absorbance vs. mole fraction of acetate.

As shown in FIG. 9, the peak absorbance increased first, then decreased once the mole fraction was bigger than 0.5. This corresponds to acetate/Fe/SA complex formula of $Fe^{3+}$ $(acetate)_m(SA)_m$, wherein m can be 1, 2, or 3.

The data suggests that with acetate concentration lower than that of SA, the absorbance will increase with acetate concentration. Once acetate concentration is higher than that of SA, the absorbance will decrease with increasing acetate concentration.

Example 11

Preparation of Acetate/Fe/SA Complex and Calibration $Fe^{3+}$ and salicylic acid ("SA") reagent ("Fe/SA reagent") was prepared by dissolving ammonium iron(III) sulfate and salicylic acid to reach final concentration of 1 mM $Fe^{3+}$ and 15 mM SA. Acetate standards were prepared by procedure analogous to that described in Example 3.

Solutions of an acetate complex of acetate, $Fe^{3+}$ and SA ("acetate/Fe/SA complex") were prepared by mixing the Fe/SA reagent solutions with aqueous solutions of acetate standards in 1:1 volume ratio. An Ocean Optics fiber optics spectrometer set up and a UV-Vis light source were used for absorbance measurement.

Figure 10:
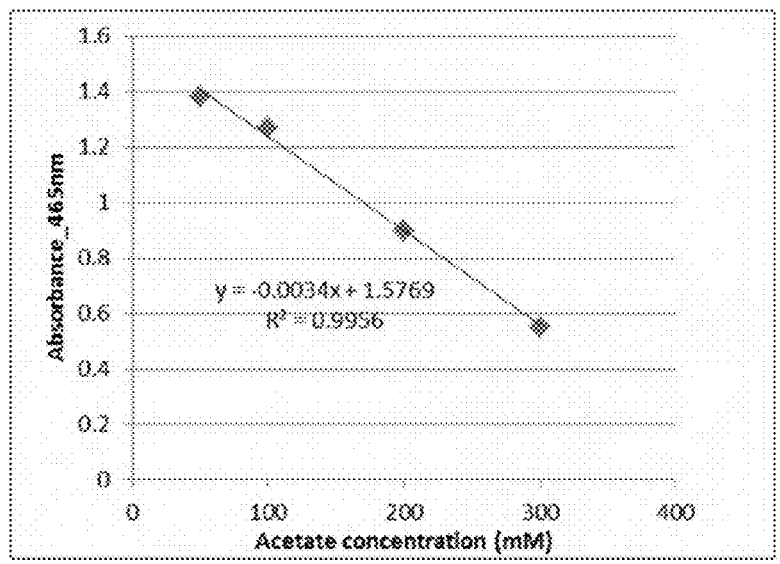
FIG. 10 shows a calibration curve of acetate standards based on the absorbance of acetate/Fe/SA complex.

For quantification of 200-300 mM acetate, a 1:1 mix of acetate solution and 1 mM $Fe^{3+}$/15 mM SA has generated a calibration curve shown in FIG. 10. There is a correlation of absorbance change vs. acetate concentration. Absorbance is linearly correlated to acetate concentration.

Example 12

Acetate/Fe/SA Complex for Acetate Quantification—Compensation for EDTA Effect in Acetate Samples If EDTA is present in aqueous solutions of acetate samples and if EDTA concentration fluctuates from sample to sample by large percentage, this may influence acetate calibration. Adding metal ions, such as $Cu^{2+}$ and/or $Zn^{2+}$, can improve Fe/SA reagent's robustness to EDTA fluctuation. The adjusted Fe/SA reagent may include: 1 mM $Fe(NH_4)(SO_4)_2$, which is a source of 1 mM $Fe^{3+}$; 200 mM salicylic acid; and 200 mM $ZnCl_2$. Another example of Fe/SA reagent may include: 1 mM $Fe(NH_4)(SO_4)_2$; 200 mM salicylic acid; and 200 mM $CuCl_2$. The Fe/SA reagent would then be mixed 1:1 in volume with an aqueous solution of acetate sample (pH 6.8-8.2). For example, 1 mL of Fe/SA reagent solution would be mixed with 1 mL of aqueous acetate sample.

Example 13

QC of Hyperpolarized Acetate

General procedures for QC of hyperpolarized imaging agents are known in the art and are described, for example in U.S. Pat. Nos. 7,803,320 and 7,519,492. These procedures could be adopted to described herein methods for QC of hyperpolarized acetate.

For example, in one embodiment, the hyperpolarized $^{13}C$ acetate sample enters into a QC appendage including a cuvette which allows for QC analysis of the product. Fe/SSA reagent can be pre-dried in the cuvette or in the flow path. Optical measurement of formed complex can be done using an LED-photodiode setup or other forms. The special QC appendage can be an extra cuvette added to existing appendage for pyruvate agent QC usage.

An offline version can be implemented as well. An Ocean Optics spectrometer or LED-photodiode setup can be used for the measurement. Fe/SSA reagent can be pre-aliquoted or dried in a cuvette, then fixed amount of dissolved $^{13}C$ acetate solution can be added to the cuvette for measurement. The formation of complex and measurement can be done in seconds, meeting the speed requirement for QC.

Figure 12:
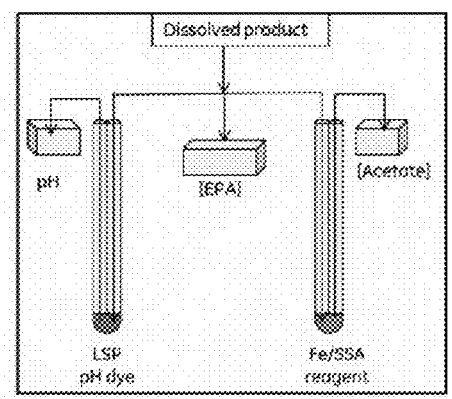
FIG. 12 shows schematics of a potential fluid path bottom plate design for hyperpolarized $^{13}C$ acetate QC.

FIG. 12 shows schematics of a potential fluid path bottom plate design for hyperpolarized $^{13}C$ acetate QC. The fluid path bottom plate contains molded TOPAS® cuvettes for absorbance/fluorescence measurement and a cylindrical holder for liquid state polarization (LSP) measurement in NMR. Electron paramagnetic agent ("EPA") is measured directly through their UV-Vis absorbance; therefore no additional reagents are needed. The received product will reach EPA cuvette first. Then the product will pass through the NMR bulbs before reaching the assay cuvettes for pH and acetate detection. The flow can happen sequentially or simultaneously. For pH measurement, the pH sensitive fluorescent dye is pre-deposited inside the tip of the NMR bulb; the received product will dissolve the dye and the mixture will reach the 1 cm path length cuvette for measurement. An additional NMR bulb/cuvette could be incorporated for holding dried Fe/SSA reagent. The received product will dissolve the Fe/SSA reagent and the mixture will reach the 1 cm path length cuvette. Thus, photometric measurement can be taken of the acetate/Fe/SSA complex for hyperpolarized $^{13}C$ acetate quantification.

While only certain features of the invention have been illustrated and described herein, many modifications and changes will occur to those skilled in the art. It is, therefore, to be understood that the appended claims are intended to cover all such modifications and changes as falling within the true spirit of the invention.

Throughout this application, various references are referred to. The disclosures of these references in their entireties are hereby incorporated by reference as if written herein.

What is claimed is:

1. A method for determining concentration of acetate in a sample, the method comprising:
    contacting the sample with $Fe^{3+}$ and an acid compound, wherein the acid compound is selected from the group consisting of sulfosalicylic acid and salicylic acid, whereby forming an acetate complex;
    wherein, when the acid compound is sulfosalicylic acid, the acetate complex comprises acetate, $Fe^{3+}$, and a compound of formula (Ia):

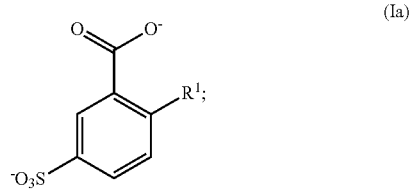

and
    wherein, when the acid compound is salicylic acid, the acetate complex comprises acetate, $Fe^{3+}$, and a compound of formula (Ib):

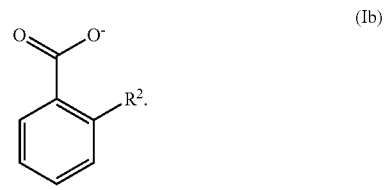

wherein
    $R^1$ is —OH or —$O^-$; and
    $R^2$ is —OH or —$O^-$; and
    photometrically measuring the acetate complex to determine concentration of acetate in the sample.

2. The method of claim 1, wherein acetate in the sample comprises $^{13}C$ hyperpolarized acetate.

3. The method of claim 2, wherein the method is performed using an apparatus designed for quality control of $^{13}C$ hyperpolarized acetate.

4. The method of claim 1, wherein the acid compound is sulfosalicylic acid, and wherein photometrically measuring comprises:
    measuring an absorbance value of the acetate complex at a light wavelength of from about 350 nm to about 550 nm; and
    determining concentration of acetate in the sample from the absorbance value of the acetate complex.

5. The method of claim 4, wherein the light wavelength is from about 430 nm to about 470 nm.

6. The method of claim 1, wherein the acid compound is salicylic acid, and wherein photometrically measuring comprises:
    measuring an absorbance value of the acetate complex at a light wavelength of from about 400 nm to about 650 nm; and
    determining concentration of acetate in the sample from the absorbance value of the acetate complex.

7. The method of claim 6, wherein the light wavelength is from about 400 nm to about 520 nm.

8. The method of claim 1, wherein the acetate complex has formula $[acetate]_{3n}[Fe^{3+}][compound\ of\ formula\ (Ia)]_n$, wherein n is an integer from 1 to 3.

9. The method of claim 1, wherein the acetate complex has formula $[acetate]_m[Fe^{3+}][compound\ of\ formula\ (Ib)]_p$, wherein m is an integer from 1 to 3 and p is an integer from 1 to 3.

10. The method of claim 1, wherein contacting the sample with $Fe^{3+}$ and the acid compound comprises contacting the sample with a reagent composition, the reagent composition comprising a $Fe^{3+}$-sulfosalicylic acid complex or $Fe^{3+}$-salicylic acid complex.

11. A method for determining concentration of $^{13}C$ hyperpolarized acetate in a sample, the method comprising:
    contacting the sample with $Fe^{3+}$ and an acid compound, wherein the acid compound is selected from the group consisting of sulfosalicylic acid and salicylic acid, whereby forming an acetate complex;
    wherein, when the acid compound is sulfosalicylic acid, the acetate complex comprises $^{13}C$ hyperpolarized acetate, $Fe^{3+}$, and a compound of formula (Ia):

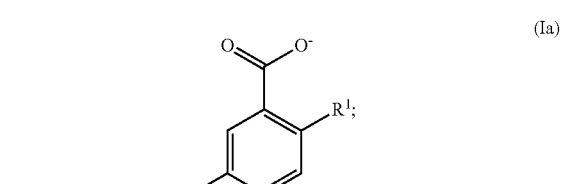

and
    wherein, when the acid compound is salicylic acid, the acetate complex comprises $^{13}C$ hyperpolarized acetate, $Fe^{3+}$, and a compound of formula (Ib):

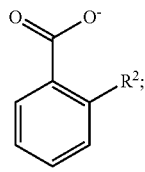

wherein
R¹ is —OH or —O⁻; and
R² is —OH or —O⁻; and
photometrically measuring the acetate complex to determine concentration of $^{13}C$ hyperpolarized acetate in the sample.

12. The method of claim 11, wherein the method is performed using an apparatus designed for quality control of $^{13}C$ hyperpolarized acetate.

13. The method of claim 11, wherein the acid compound is sulfosalicylic acid, and wherein photometrically measuring comprises:
measuring an absorbance value of the acetate complex at a light wavelength of from about 350 nm to about 550 nm; and
determining concentration of $^{13}C$ hyperpolarized acetate in the sample from the absorbance value of the acetate complex.

14. The method of claim 13, wherein the light wavelength is from about 430 nm to about 470 nm.

15. The method of claim 11, wherein the acid compound is salicylic acid, and wherein photometrically measuring comprises:
measuring an absorbance value of the acetate complex at a light wavelength of from about 400 nm to about 650 nm; and
determining concentration of $^{13}C$ hyperpolarized acetate in the sample from the absorbance value of the acetate complex.

16. The method of claim 15, wherein the light wavelength is from about 400 nm to about 520 nm.

17. The method of claim 11, wherein the acetate complex has formula [$^{13}C$ hyperpolarized acetate]$_{3n}$[$Fe^{3+}$][compound of formula (Ia)]$_n$, wherein n is an integer from 1 to 3.

18. The method of claim 11, wherein the acetate complex has formula [$^{13}C$ hyperpolarized acetate]$_m$[$Fe^{3+}$][compound of formula (Ib)]$_p$, wherein m is an integer from 1 to 3 and p is an integer from 1 to 3.

19. The method of claim 11, wherein contacting the sample with $Fe^{3+}$ and the acid compound comprises contacting the sample with a reagent composition, the reagent composition comprising a $Fe^{3+}$-sulfosalicylic acid complex or $Fe^{3+}$-salicylic acid complex.

* * * * *